United States Patent
Futatsugi et al.

(10) Patent No.: US 10,729,638 B2
(45) Date of Patent: Aug. 4, 2020

(54) POWDER HAIR DYE COMPOSITION

(71) Applicant: HOYU CO., LTD., Aichi (JP)

(72) Inventors: Shizuka Futatsugi, Aichi (JP); Yoshiyuki Uesawa, Aichi (JP); Jun Matsubayashi, Aichi (JP); Hiromi Umino, Aichi (JP)

(73) Assignee: HOYU CO., LTD., Aichi (JP)

( * ) Notice: Subject to any disclaimer, the term of this patent is extended or adjusted under 35 U.S.C. 154(b) by 0 days.

(21) Appl. No.: 16/309,917

(22) PCT Filed: Jun. 9, 2017

(86) PCT No.: PCT/JP2017/021519
§ 371 (c)(1),
(2) Date: Dec. 13, 2018

(87) PCT Pub. No.: WO2017/217338
PCT Pub. Date: Dec. 21, 2017

(65) Prior Publication Data
US 2019/0328646 A1  Oct. 31, 2019

(30) Foreign Application Priority Data
Jun. 15, 2016 (JP) .................. 2016-119255

(51) Int. Cl.
A61K 8/02 (2006.01)
A61K 8/73 (2006.01)
A61K 8/19 (2006.01)
A61K 8/34 (2006.01)
A61K 8/41 (2006.01)
A61Q 5/10 (2006.01)

(52) U.S. Cl.
CPC ............ A61K 8/73 (2013.01); A61K 8/022 (2013.01); A61K 8/19 (2013.01); A61K 8/347 (2013.01); A61K 8/415 (2013.01); A61Q 5/10 (2013.01); A61K 2800/432 (2013.01); A61K 2800/51 (2013.01); A61K 2800/59 (2013.01); A61K 2800/882 (2013.01)

(58) Field of Classification Search
None
See application file for complete search history.

(56) References Cited

U.S. PATENT DOCUMENTS

| 2010/0064449 A1* | 3/2010 | Khan ............... A61K 8/22 8/407 |
| 2011/0203604 A1* | 8/2011 | Hasegawa .......... A61K 8/22 132/208 |
| 2012/0207689 A1 | 8/2012 | Konno et al. |

FOREIGN PATENT DOCUMENTS

| EP | 2361604 A1 | 8/2011 |
| JP | 2006-273759 A | 10/2006 |
| JP | 3990545 B2 | 10/2007 |
| JP | 2010-260837 A | 11/2010 |
| JP | 2011-93823 A | 5/2011 |
| JP | 2011-105620 A | 6/2011 |
| WO | 2009/064061 A1 | 5/2009 |
| WO | 2015/052757 | 4/2015 |
| WO | WO-2015052757 A1 * | 4/2015 |

OTHER PUBLICATIONS

Corrosionpedia—What is a Sequestering agent?, accessed Sep. 20, 2019 (Year: 2019).*
WIPO, International Search Report for International Patent Application No. PCT/2017/021519, dated Aug. 29, 2017.
EPO, Extended European Search Report for European Patent Application No. 17813235.2, dated Jan. 24, 2020.

* cited by examiner

Primary Examiner — Robert A Wax
Assistant Examiner — Melissa S Mercier

(57) ABSTRACT

The purpose of the present invention is to solve the problem, in powder hair dye compositions that contain a percarbonate, that a change occurs in the dyed color tone before and after storage when the composition contains metaaminophenol, 5-aminoorthocresol, resorcin, or a salt thereof, as an oxidation dye. To solve the aforementioned problem, a powder hair dye composition containing (A) a percarbonate, (B) a starch, and (C) an oxidation dye is provided, characterized in that the composition contains at least 7 mass % starch (B) and in that the oxidation dye (C) contains at least one selected from metaaminophenol, 5-aminoorthocresol, resorcin, and salts thereof. Thus, a powder hair dye composition can be obtained which suppresses change in the dye color tone before and after storage and which has excellent storage stability.

11 Claims, No Drawings

POWDER HAIR DYE COMPOSITION

TECHNICAL FIELD

The present invention relates to a powder hair dye composition for dyeing hair and the like. More specifically, the invention relates to a powder hair dye composition which suppresses a time dependent change in the dyed color tone in long-term storage by blending a certain amount or more of starch in the composition.

BACKGROUND ART

Hair dye compositions are those for dyeing hair by oxidizing an oxidation dye and developing a color on the hair. Among the hair dye compositions, a powder hair dye is known which is in a powder form and is mixed with a liquid medium such as water and then applied to the hair to dye the hair.

For example, Patent Document 1 discloses that starch is blended in a powder hair dye in order to maintain the stability of a solid oxidizing agent (such as sodium percarbonate) before and after storage, Patent Document 2 discloses that excellent hair dyeing power is exerted and the hair can be dyed in a vivid warm color tone by blending a percarbonate salt and a specific dye intermediate such as 5-amino-o-cresol sulfate, and Patent Document 3 discloses that favorable operability and temporal stability are exerted by blending a thickener such as sodium percarbonate and sodium carboxymethyl cellulose.

CITATION LIST

Patent Document

Patent Document 1: JP 2006-273759 A
Patent Document 2: JP 2010-260837 A
Patent Document 3: WO 2015/052757 A

SUMMARY OF THE INVENTION

Problem to be Solved by the Invention

In powder hair dye compositions that contain a percarbonate, there has been a problem that a change occurs in the dyed color tone before and after storage when the compositions contain m-aminophenol, 5-amino-o-cresol, resorcin, or a salt thereof as an oxidation dye. Accordingly, an object of the invention is to suppress a change in the dyed color tone before and after storage in the above-mentioned powder hair dye compositions that contain a specific oxidation dye.

Means for Solving Problem

As a result of intensive investigations on the above-mentioned problem, the inventors have found out that a change is suppressed in the dyed color tone before and after storage by blending a certain amount or more of starch in the above-mentioned powder hair dye compositions that contain a specific oxidation dye and thus have completed the invention.

In other words, the invention is the following powder hair dye composition and a method of using the same.

The powder hair dye composition of the invention is a powder hair dye composition which contains (A) a percarbonate, (B) a starch, and (C) an oxidation dye and in which the powder hair dye composition contains (B) the starch at 7 mass % or more and (C) the oxidation dye contains at least one selected from m-aminophenol, 5-amino-o-cresol, resorcin, or a salt of m-aminophenol, 5-amino-o-cresol, or resorcin.

According to this powder hair dye composition, it is possible to provide a powder hair dye composition which suppresses a time dependent change in the dyed color tone before and after storage and has excellent storage stability. In addition, by setting the content of starch to 7 mass % or more, an effect is exerted that not only a change is suppressed in the dyed color tone but it is also possible to prepare a hair dye coating liquid having excellent coating operability when the powder hair dye composition is mixed with a liquid medium such as water.

In addition, according to an embodiment of the powder hair dye composition of the invention, a mass ratio (A/B) of (A) the percarbonate to (B) the starch is from 0.1 to 10.

According to this feature, it is possible to further exert the effect of the invention that a time dependent change is suppressed in the dyed color tone before and after storage.

Furthermore, according to an embodiment of the powder hair dye composition of the invention, the powder hair dye composition contains (D) a chelating agent at from 1 to 5 mass %.

According to this feature, it is possible to exert an effect of enhancing the feel of the hair at the time of finishing.

Furthermore, according to an embodiment of the powder hair dye composition of the invention, the powder hair dye composition contains (E) a water-soluble polymer compound (excluding starch) at from 1 to 50 mass %.

According to this feature, it is possible to exert an effect of having excellent coating operability.

Furthermore, according to an embodiment of the powder hair dye composition of the invention, the powder hair dye composition further contains (D) a chelating agent and (E) a water-soluble polymer compound (excluding starch), the powder hair dye composition contains (A) the percarbonate at 15 mass % or more, (D) the chelating agent at from 1 to 3 mass %, and (E) the water-soluble polymer compound (excluding starch) at from 5 to 50 mass %, (E) the water-soluble polymer compound (excluding starch) contains xanthan gum at from 5 to 15 mass %, and a mass ratio (B/D) of (B) the starch to (D) the chelating agent is 4.0 or more.

According to this feature, it is possible to provide a powder hair dye composition which has not only an excellent effect of suppressing a change in the dyed color tone before and after storage but also excellent coating operability and feel at the time of finishing.

The method of using a powder hair dye composition of the invention includes a step of mixing the powder hair dye composition of the invention with a liquid medium to prepare a hair dye coating liquid and a step of applying the hair dye coating liquid to hair.

According to this method of using a powder hair dye composition, it is possible to prepare a hair dye coating liquid having excellent coating operability and it is thus possible to provide a method of hair dyeing treatment in which color unevenness is suppressed and the levelness of dyeing is excellent.

Effect of the Invention

According to the invention, it is possible to provide a powder hair dye composition which suppresses a time dependent change in the dyed color tone before and after storage and has excellent storage stability in powder hair dye compositions that contain m-aminophenol, 5-amino-o-cresol, resorcin, or a salt thereof as an oxidation dye.

MODE(S) FOR CARRYING OUT THE INVENTION

Next, the invention will be described including the best modes for carrying out the invention.
[Powder Hair Dye Composition]

The powder hair dye composition of the invention is a powder hair dye composition which contains (A) a percarbonate, (B) a starch, and (C) an oxidation dye and in which the powder hair dye composition contains (B) the starch at 7 mass % or more and (C) the oxidation dye contains at least one selected from m-aminophenol, 5-amino-o-cresol, resorcin, or a salt of m-aminophenol, 5-amino-o-cresol, or resorcin.

The powder hair dye composition of the invention is used for the purpose of dyeing the hair and is an oxidation hair dye which contains at least an oxidizing agent and an oxidation dye. When the oxidation hair dye acts on the hair, the oxidation dye develops a color by the action of the oxidizing agent and the hair is dyed in the desired color tone. Incidentally, a direct dye may be blended in the oxidation hair dye for adjustment of the color tone of dyed hair.

The powder hair dye composition of the invention is a powder preparation of a hair dye composition, and the respective components such as an oxidizing agent and an oxidation dye are also blended in a powder form. The powder hair dye composition is usually a one-component type but may be a multi-component type of a two- or more-component type. The powder hair dye composition is applied to the hair by being mixed with a liquid medium such as water and thus prepared into a hair dye coating liquid at the time of use.

Next, the respective components to be used in the powder hair dye composition of the invention will be described in detail. Incidentally, the contents of the respective components indicate the contents of the respective agents in the mixture before being mixed with the liquid medium in the case of preparing the powder hair dye composition into a multi-component type.

<(A) Percarbonate>

A percarbonate is an oxidizing agent and has an action of oxidizing the oxidation dye to develop a color and an action of decomposing melanin inside the hair. Specific examples thereof may include sodium percarbonate and potassium percarbonate. Among these, sodium percarbonate is preferable.

The content of percarbonate in the powder hair dye composition is not particularly limited, but it is, for example, from 15 to 60 mass %, and the lower limit thereof is preferably 20 mass % or more and more preferably 25 mass % or more, and the upper limit thereof is preferably 50 mass % or less and more preferably 40 mass % or less. When the content of percarbonate is 15 mass % or more, the effect of the invention is further exerted that a change is suppressed in the dyed color tone in long-term storage, and further, the fluidity of the powder hair dye composition is also improved. On the other hand, when the content of percarbonate is 50 mass % or less, an effect is exerted that the hair is hardly damaged.

The powder hair dye composition of the invention may contain an optional oxidizing agent in addition to (A) the percarbonate. Examples of the optional oxidizing agent may include various kinds of peroxide salts, hydrogen peroxide adducts of various kinds of sulfates, hydrogen peroxide adducts of various kinds of phosphates, hydrogen peroxide adducts of various kinds of pyrophosphates, urea peroxide, melamine peroxide, various kinds of perborates, various kinds of perbromates, and various kinds of permanganates.

In the case of concurrently using (A) the percarbonate and an optional oxidizing agent, the content of the optional oxidizing agent is preferably 5 mass % or less from the viewpoint of imparting a deep color tone to the hair after finishing. In addition, the total content of the oxidizing agents is preferably 60 mass % or less from the viewpoint of improving the temporal stability of the oxidizing agents in the case of being stored for a long period of time.

<(B) Starch>

A starch is a water-soluble polymer compound containing amylose and amylopectin as a main component and also includes modified starches which have been physically or chemically modified to have improved functional properties in addition to natural starches. Specific examples thereof may include rice starch, potato starch, sweet potato starch, corn starch, tapioca starch, and wheat starch. Potato starch, rice starch, and corn starch are preferable and potato starch is more preferable. These can be used singly or in combination of two or more kinds thereof.

The content of starch in the powder hair dye composition of the invention is 7 mass % or more and more preferably 10 mass % or more. By setting the content of starch to be in the above range, it is possible to suppress a change in the dyed color tone in long-term storage. In addition, it is possible to prepare a hair dye coating liquid having excellent coating operability when the powder hair dye composition is mixed with a liquid medium such as water. Furthermore, it is possible to improve the feel of the hair at the time of finishing.

The upper limit value of the content of starch in the powder hair dye composition is not particularly limited, but it is preferably 50 mass % or less, more preferably 40 mass % or less, still more preferably 30 mass % or less, and particularly preferably 20 mass % or less. When the content of starch is 50 mass % or less, the fluidity of the powder hair dye composition is improved. In addition, there is also an advantage that the scattering property is diminished and the productivity is improved.

In addition, the mass ratio (A/B) of (A) the percarbonate to (B) the starch is not particularly limited, but it is preferably from 0.1 to 10 from the viewpoint of further exerting the effect of the invention that a change is suppressed in the dyed color tone in long-term storage. The lower limit value thereof is more preferably 0.3 or more and particularly preferably 0.5 or more. The upper limit value thereof is more preferably 8 or less and particularly preferably 5 or less.

<(C) Oxidation Dye>

The oxidation dye is a dye which is oxidatively polymerized by (A) the percarbonate and develops a color.

The oxidation dye includes a dye intermediate and a coupler, and the dye intermediate is a substance which develops a color by the oxidation of itself and the coupler is a substance to exhibit various color tones in combination with dye intermediates.

The dye intermediate is a dye precursor which is mainly an o- or p-phenylenediamine or an aminophenol and itself is usually a colorless or weakly colored compound.

Specific examples thereof may include p-aminophenol, o-aminophenol, p-methylaminophenol, p-phenylenediamine, toluene-2,5-diamine, N-phenyl-p-phenylenediamine, 4,4'-diaminodiphenylamine, 2-hydroxyethyl-p-phenylenediamine, o-chloro-p-phenylenediamine, 4-amino-m-cresol, 2-amino-4-hydroxyethylaminoanisole, 2,4-diaminophenol, 2,2'-[(4-aminophenyl)imino]bisethanol, and salts such as sulfates and hydrochlorides thereof.

As the kind of dye intermediate, one kind or two or more kinds can be selected and used depending on the desired color tone of the hair. In addition, the content thereof is not particularly limited, but it is, for example, from 1 to 30 mass % in the powder hair dye composition, the lower limit value thereof is more preferably 5 mass % or more, and the upper limit value thereof is more preferably 20 mass % or less.

Examples of the coupler may mainly include m-diamines, m-aminophenols, or m-diphenols, and specific examples thereof may include m-aminophenol, 5-amino-o-cresol, resorcin, catechol, pyrogallol, phloroglucin, gallic acid, hydroquinone, 5-(2-hydroxyethylamino)-2-methylphenol, m-phenylenediamine, 2,4-diaminophenoxyethanol, toluene-3,4-diamine, α-naphthol, 2,6-diaminopyridine, diphenylamine, 3,3'-iminodiphenyl, 1,5-dihydroxynaphthalene, tannic acid, 1-hydroxyethyl-4,5-diamino pyrazole, and salts such as sulfates and hydrochlorides thereof.

As the kind of coupler, one kind or two or more kinds can be selected and used depending on the desired color tone of the hair. In addition, the content thereof is not particularly limited, but it is, for example, from 0.1 to 20 mass % in the powder hair dye composition, the lower limit value thereof is more preferably 0.5% by mass or more and particularly preferably 1% by mass or more. The upper limit value thereof is more preferably 15 mass % or less and particularly preferably 10 mass % or less.

The powder hair dye composition of the invention contains at least one selected from m-aminophenol, 5-amino-o-cresol, resorcin, or a salt thereof as (C) the oxidation dye.

m-Aminophenol m-Aminophenol is a compound represented by the following Chemical Formula (1) (CAS Number: 591-27-5).

[Chem. 1]

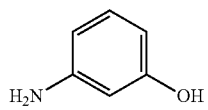

化 (1)

Chemical Formula (1)

5-Amino-o-cresol 5-Amino-o-cresol is a compound represented by the following Chemical Formula (2) (CAS Number: 2835-95-2).

[Chem. 2]

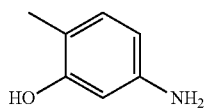

化 (2)

Chemical Formula (2)

Resorcin

Resorcin is a compound represented by the following Chemical Formula (3) (CAS Number: 108-46-3).

[Chem. 3]

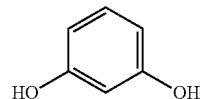

化 (3)

Chemical Formula (3)

<(D) Chelating Agent>

It is preferable that the powder hair dye composition of the invention contains (D) a chelating agent. The chelating agent is a substance which captures a metal ion, and examples thereof may include L-aspartic acid N,N-diacetic acid tetrasodium salt, alanine, ethylenediamine hydroxyethyl triacetic acid trisodium salt, edetic acid, disodium edetate, edetate calcium disodium, trisodium edetate, tetrasodium edetate, sodium citrate, gluconic acid, L-glutamic acid diacetic acid tetrasodium salt, tartaric acid, phytic acid, sodium polyphosphate, and sodium metaphosphate, and ethylenediamine hydroxyethyl triacetic acid trisodium salt, disodium edetate, and tetrasodium edetate are preferable and ethylenediamine hydroxyethyl triacetic acid trisodium salt is more preferable. By containing a chelating agent, it is possible to exert the effect of enhancing the feel of the hair at the time of finishing.

The content of chelating agent in the powder hair dye composition is preferably from 1 to 5 mass %. The lower limit value thereof is more preferably 1.2 mass % or more, still more preferably 1.5 mass % or more, and particularly preferably 1.7 mass % or more. The upper limit value thereof is more preferably 4.5 mass % or less, still more preferably 4 mass % or less, and particularly preferably 3 mass % or less. In a case in which the content of chelating agent is in the above range, it is possible to further exert the effect by the action of chelating agent that the feel of the hair is enhanced at the time of finishing while exerting the effect of the invention that a change is suppressed in the dyed color tone.

In addition, the mass ratio (B/D) of (B) the starch to (D) the chelating agent is not particularly limited, but it is preferably 3.0 or more and more preferably 4.0 or more from the viewpoint of further exerting the effect of the invention that a change is suppressed in the dyed color tone in long-term storage. In addition, the mass ratio (B/D) is preferably 15 or less and more preferably 12 or less from the viewpoint of improving the fluidity of the powder hair dye composition.

<(E) Water-Soluble Polymer Compound>

It is preferable that the powder hair dye composition of the invention contains (E) a water-soluble polymer compound (excluding starch. Hereinafter, simple description of "water-soluble polymer compound" means to exclude starch.). By containing a water-soluble polymer compound, it is possible to adjust the viscosity of the hair dye coating liquid and thus to improve ease of handling the hair dye coating liquid with a brush, spreading and adhesive property of the hair dye coating liquid to the hair.

Specific examples of the water-soluble polymer compound may include a natural polymer, a semisynthetic polymer, a synthetic polymer, and an inorganic polymer. Examples of a natural water-soluble polymer compound may include seaweed extracts such as alginic acid, carrageenan, agar, and furcellaran, seed mucilage such as guar gum, quince seed, konjak mannan, tamarind gum, tara gum, dextrin, and locust bean gum, sap mucilage such as gum arabic, gum ghatti, gum karaya, and gum tragacanth, fruit mucilage such as arabinogalactan, pectin, and quince, plant-based proteins such as wheat protein and soybean protein, animal-based proteins such as albumin, casein, gelatin, and collagen, mucilage produced by microorganisms such as curdlan, xanthan gum, gellan gum, cyclodextrin, dextran, pullulan, and succinoglucan, and mucopolysaccharides such as chitosan and hyaluronic acid.

Examples of the semisynthetic water-soluble polymer compound may include methyl cellulose, ethyl cellulose, hydroxyethyl cellulose, hydroxypropyl cellulose, carboxymethyl cellulose, sodium carboxymethyl cellulose, methyl hydroxypropyl cellulose, cationized cellulose, alginic acid propylene glycol ester, and an alginate (for example, sodium alginate).

Examples of the synthetic water-soluble polymer compound may include polyvinyl alcohol, polyvinyl pyrrolidone, polyvinyl methyl ether, carboxyvinyl polymer, sodium polyacrylate, polyacrylamide, polyethylene oxide, an ethylene oxide-propylene oxide block copolymer, and an acrylic acid-alkyl acrylate copolymer. In addition to these, examples thereof may also include a copolymer composed of a half ester of itaconic acid with polyoxyethylene alkyl ether or an ester of methacrylic acid with polyoxyethylene alkyl ether and at least one monomer selected from acrylic acid, methacrylic acid, or an alkyl ester thereof.

The content of the water-soluble polymer compound in the powder hair dye composition is not particularly limited, but it is preferably from 1 to 50 mass %. The lower limit value thereof is more preferably 5 mass % or more, still more preferably 10 mass % or more, and particularly preferably 20 mass % or more. The upper limit value thereof is more preferably 40 mass % or less, still more preferably 30 mass % or less, and particularly preferably 25 mass % or less. In a case in which the content of the water-soluble polymer compound is in the above range, it is possible to improve coating operability such as ease of handling the hair dye coating liquid with a brush.

Furthermore, from the viewpoint of improving the mixing property with the liquid medium such as water, the operability at the time of application to the hair, and the temporal stability in the case of being stored for a long period of time in a well-balanced manner, preferred examples of the water-soluble polymer compound may include sodium carboxymethyl cellulose, xanthan gum, hydroxyethyl cellulose, and a cationized polymer, and xanthan gum is particularly preferable.

In particular, the content of xanthan gum is preferably from 1 to 20 mass %. The lower limit value thereof is more preferably 3 mass % or more and still more preferably 5 mass % or more. The upper limit value thereof is more preferably 15 mass % or less and still more preferably 10 mass % or less. When the content of xanthan gum is 20 mass % or less, coating operability such as ease of handling the hair dye coating liquid with a brush and the feel of the hair at the time of finishing are improved.

In addition, the ratio (A/(B+D+E)) of the mass of (A) the percarbonate to the total mass of (B) the starch, (D) the chelating agent, and (E) the water-soluble polymer compound in the powder hair dye composition of the invention is not particularly limited, but it is preferably from 0.2 to 1.2.

By adjusting the mass ratio of the respective components to be in the above range, it is possible to exert an excellent effect in all items of suppression of a change in the dyed color tone in long-term storage, fluidity, improvement in the coating operability, and feel of the hair at the time of finishing.

<Other Components>

The powder hair dye composition of the invention may contain optional components in addition to the components (A) to (E) described above, if necessary.

Examples of the other components may include an alkali agent, a dispersant, a direct dye, an oil component, a surfactant, an inorganic salt, a pH adjusting agent, a saccharide, a hair growth component, a plant extract, a herbal medicine extract, an amino acid-polypeptide, vitamins, a perfume, a preservative, and an ultraviolet absorber.

<Alkali Agent>

The alkali agent has an action of expanding the hair and thus promoting permeation of the dye and oxidizing agent into the hair. Examples of the alkali agent may include a silicate, a carbonate, a hydrogencarbonate, a metasilicate, a phosphate, a basic amino acid, and a hydroxide. Specific examples of the silicate may include sodium silicate and potassium silicate, examples of the carbonate may include sodium carbonate, ammonium carbonate, magnesium carbonate, and guanidine carbonate, examples of the hydrogencarbonate may include sodium hydrogencarbonate, and ammonium hydrogencarbonate, examples of the metasilicate may include sodium metasilicate and potassium metasilicate, examples of the phosphate may include primary ammonium phosphate, secondary ammonium phosphate, disodium hydrogenphosphate, and trisodium phosphate, examples of the basic amino acid may include arginine, lysine, and a salt thereof, and examples of the hydroxide may include calcium hydroxide and magnesium hydroxide.

<Dispersant>

Examples of the dispersant may include a metal salt of stearic acid such as magnesium stearate, silicic acid, a metal salt of silicic acid, talc, sucrose fatty acid ester, lactose, and silica, and magnesium stearate is particularly preferable. By containing a dispersant, it is possible to improve the fluidity of the powder hair dye composition.

The content of the dispersant in the powder hair dye composition is not particularly limited, but it is preferably from 0.01 to 10 mass %. The lower limit value thereof is more preferably 0.1 mass % or more and still more preferably 0.5 mass % or more. The upper limit value thereof is more preferably 5 mass % or less and still more preferably 2 mass % or less.

<Direct Dye>

The direct dye is a compound exhibiting a color and is a dye which adheres to or permeates the hair to dye the hair. Examples thereof may include an acidic dye, a basic dye, a natural dye, a nitro dye, a HC dye, and a disperse dye. These direct dyes may be blended singly or in combination.

Examples of the acidic dye may include Red No. 2, Red No. 3, Red No. 102, Red No. 104 (1), Red No. 105 (1), Red No. 106, Red No. 227, Red No. 230 (1), Yellow No. 4, Yellow No. 5, Yellow No. 202 (1), Yellow No. 202 (2), Yellow No. 203, Orange No. 205, Orange No. 207, Orange No. 402, Green No. 3, Green No. 204, Green No. 401, Purple No. 401, Blue No. 1, Blue No. 2, Blue No. 202, Brown No. 201, and Black No. 401.

Examples of the basic dye may include Basic Blue 3, Basic Blue 6, Basic Blue 7, Basic Blue 9, Basic Blue 26, Basic Blue 41, Basic Blue 47, Basic Blue 99, Basic Brown 4, Basic Brown 16, Basic Brown 17, Basic Green 1, Basic Green 4, Basic Orange 1, Basic Orange 2, Basic Orange 31, Basic Red 1, Basic Red 2, Basic Red 22, Basic Red 46, Basic Red 51, Basic Red 76, Basic Red 118, Basic Violet 1, Basic Violet 3, Basic Violet 4, Basic Violet 10, Basic Violet 11: 1, Basic Violet 14, Basic Violet 16, Basic Yellow 11, Basic Yellow 28, Basic Yellow 57, and Basic Yellow 87.

Examples of the natural dye may include gardenia pigment, turmeric pigment, annatto pigment, sodium copper chlorophyllin, paprika pigment, lac pigment, and henna.

Examples of the nitro dye may include 4-nitro-o-phenylenediamine, 2-nitro-p-phenylenediamine, 2-amino-4-nitrophenol, 2-amino-5-nitrophenol, picramic acid, picric acid, and a salt thereof.

Examples of the HC dye may include HC Blue No. 2, HC Blue No. 5, HC Blue No. 6, HC Blue No. 9, HC Blue No. 10, HC Blue No. 11, HC Blue No. 12, HC Blue No. 13, HC Orange No. 1, HC Orange No. 2, HC Orange No. 3, HC Red No. 1, HC Red No. 3, HC Red No. 7, HC Red No. 10, HC Red No. 11, HC Red No. 13, HC Red No. 14, HC Violet No. 1, HC Violet No. 2, HC Yellow No. 2, HC Yellow No. 4, HC Yellow No. 5, HC Yellow No. 6, HC Yellow No. 9, HC Yellow No. 10, HC Yellow No. 11, HC Yellow No. 12, HC Yellow No. 13, HC Yellow No. 14, and HC Yellow No. 15.

Examples of the disperse dye may include Disperse Black 9, Disperse Blue 1, Disperse Blue 3, Disperse Blue 7, Disperse Brown 4, Disperse Orange 3, Disperse Red 11, Disperse Red 15, Disperse Red 17, Disperse Violet 1, Disperse Violet 4, and Disperse Violet 15.

<Oil Component>

Examples of the oil component may include a higher alcohol, fats and oils, waxes, a hydrocarbon, a higher fatty acid, esters, silicone oil, and fluorine oil. One kind or two or more kinds can be selected from these oil components and used.

Examples of the higher alcohol may include cetyl alcohol (cetanol), stearyl alcohol, cetostearyl alcohol, oleyl alcohol, linoleyl alcohol, linolenyl alcohol, arachyl alcohol, behenyl alcohol, lauryl alcohol, myristyl alcohol, 2-hexyldecanol, isostearyl alcohol, 2-octyldodecanol, decyltetradecanol, phytosterol, phytostanol, cholesterol, cholestanol, lanosterol, and ergosterol.

Fats and oils are triglycerides, namely triesters of fatty acids with glycerin. Examples thereof may include olive oil, rose hip oil, camellia oil, Shea butter, macadamia nut oil, almond oil, tea seed oil, sasanqua oil, safflower oil, sunflower oil, soybean oil, cottonseed oil, sesame oil, beef tallow, cacao butter, corn oil, peanut oil, rapeseed oil, rice bran oil, rice germ oil, wheat germ oil, pearl barley oil, grape seed oil, avocado oil, carrot oil, castor oil, linseed oil, coconut oil, mink oil, and egg yolk oil.

A hydrocarbon is a compound composed of carbon and hydrogen. Examples thereof may include liquid paraffin, paraffin, microcrystalline wax, petroleum jelly, isoparaffins, ozokerite, ceresin, polyethylene, α-olefin oligomer, polybutene, synthetic squalane, squalene, hydrogenated squalane, limonene, and turpentine oil.

Examples of the higher fatty acid may include lauric acid, myristic acid, palmitic acid, stearic acid, behenic acid, isostearic acid, hydroxystearic acid, 12-hydroxystearic acid, oleic acid, undecylenic acid, linoleic acid, ricinoleic acid, and lanolin fatty acid.

Esters are compounds obtained by the dehydration reaction of fatty acids with alcohols. Examples thereof may include diisopropyl adipate, 2-hexyldecyl adipate, isopropyl myristate, myristyl myristate, cetyl octanoate, cetyl isooctanoate, isononyl isononanoate, diisopropyl sebacate, isopropyl palmitate, 2-ethylhexyl palmitate, cetyl ethylhexanoate, butyl stearate, isocetyl isostearate, hexyl laurate, decyl oleate, fatty acid (C10-30) (cholesteryl/lanosteryl), lauryl lactate, octyldodecyl lactate, lanolin acetate, dipentaerythritol fatty acid ester, monoisostearic acid N-alkyl glycol, and a lanolin derivative.

A silicone oil is a synthetic polymer in which silicon to which an organic group is attached and oxygen are alternately connected to each other by a chemical bond. Examples thereof may include dimethylpolysiloxane (INCI name: dimethicone), dimethyl polysiloxane having a hydroxyl end group (INCI name: dimethiconol), methylphenyl polysiloxane, decamethylcyclopentasiloxane, dodecamethylcyclohexasiloxane, polyether-modified silicone, highly polymerized silicone having an average polymerization degree of from 650 to 10000, amino-modified silicone, betaine-modified silicone, alkyl-modified silicone, alkoxy-modified silicone, mercapto-modified silicone, carboxy-modified silicone, and fluorine-modified silicone.

Among these, examples of the amino-modified silicone may include an aminopropylmethylsiloxane-dimethylsiloxane copolymer (INCI name: aminopropyl dimethicone), an aminoethylaminopropylsiloxane-dimethylsiloxane copolymer (INCI name: amodimethicone), and an aminoethylaminopropylmethylsiloxane-dimethylsiloxane copolymer (INCI name: trimethylsilylamodimethicone).

<Surfactant>

Examples of the surfactant may include a nonionic surfactant, a cationic surfactant, an anionic surfactant, and an amphoteric surfactant.

Incidentally, in the following description, POE represents a polyoxyethylene chain, POP represents a polyoxypropylene chain, and the number in parentheses following this indicates the number of moles added. In addition, the number in parentheses following alkyl indicates the number of carbon atoms in the fatty acid chain.

Examples of the nonionic surfactant may include a POE alkyl ether, a POE alkyl phenyl ether, a POE-POP alkyl ether, a POE sorbitan fatty acid ester, a POE mono fatty acid ester, a POE glycerin fatty acid ester, a polyglycerin fatty acid ester, a monoglycerin fatty acid ester, a sorbitan fatty acid ester, a sucrose fatty acid ester, and an alkyl polyglucoside. Specific examples of the POE alkyl ether may include POE lauryl ether, POE cetyl ether, POE stearyl ether, POE behenyl ether, POE lanolin, and POE phytosterol.

Examples of the cationic surfactant may include an alkyl quaternary ammonium salt such as a monoalkyl type quaternary ammonium salt, a dialkyl type quaternary ammonium salt, a trialkyl type quaternary ammonium salt, a benzalkonium type quaternary ammonium salt or a monoalkyl ether type quaternary ammonium salt, an amine salt such as an alkylamine salt, a fatty acid amidoamine salt, an ester-containing tertiary amine salt, or an arcobel type tertiary amine salt, a cyclic quaternary ammonium salt such as an alkyl pyridinium salt or an alkyl isoquinolinium salt, and benzethonium chloride.

The cationic surfactant is preferably an alkyl quaternary ammonium salt, more preferably a monoalkyl type quaternary ammonium salt or a dialkyl type quaternary ammonium salt, and particularly preferably a monoalkyl type quaternary ammonium salt.

Examples of the monoalkyl type quaternary ammonium salt may include lauryltrimethylammonium chloride, lauryltrimethylammonium bromide, alkyl (16,18) trimethylammonium chloride, cetyltrimethylammonium chloride, cetyltrimethylammonium bromide, cetyltrimethylammonium saccharin, stearyltrimethylammonium chloride, stearyltrimethylammonium bromide, behenyltrimethylammonium chloride, stearyltrimethylammonium saccharin, alkyl (28) trimethylammonium chloride, diPOE (2) oleylmethylammonium chloride, diPOEstearylmethylammonium chloride, POE (1) POP (25) diethylmethylammonium chloride, POP methyldiethylammonium chloride, methacryloyloxyethyltrimethylammonium chloride, and behenyltrimethylammonium methyl sulfate. The monoalkyl type quaternary ammonium salt is particularly preferably stearyltrimethylammonium chloride, alkyl (16,18) trimethylammonium chloride, and cetyltrimethylammonium chloride.

Examples of the anionic surfactant may include an alkyl ether sulfate, a POE alkyl ether sulfate, an alkyl sulfate, an alkenyl ether sulfate, an alkenyl sulfate, an olefin sulfonate, an alkane sulfonate, a saturated or unsaturated fatty acid salt, an alkyl or alkenyl ether carboxylate, an α-sulfone fatty acid salt, a N-acylamino acid type surfactant, a phosphoric acid mono- or diester type surfactant, and a sulfosuccinic acid ester. The counter ion of the anion group in these surfactants may be, for example, any of a sodium ion, a potassium ion, or triethanolamine.

More specific examples thereof may include disodium lauryl sulfosuccinate, sodium lauryl sulfate, sodium myristyl sulfate, potassium lauryl sulfate, ammonium lauryl sulfate, triethanolamine lauryl sulfate, sodium cetyl sulfate, sodium stearyl sulfate, sodium POE lauryl ether sulfate, triethanolamine POE lauryl ether sulfate, ammonium POE lauryl ether sulfate, sodium POE stearyl ether sulfate, disodium lauryl sulfosuccinate, sodium methyl stearoyl taurate, triethanolamine dodecylbenzenesulfonate, sodium tetradecene sulfonate, sodium lauryl phosphate, POE lauryl ether phosphoric acid and a salt thereof, N-lauroyl glutamic acid salts (sodium lauroyl glutamate and the like), a N-lauroylmethyl-β-alanine salt, a N-acylglycine salt, a N-acylglutamate, lauric acid and myristic acid which are a higher fatty acid, and a salt of these higher fatty acids, and one kind or two or more kinds of these can be used.

Examples of the amphoteric surfactant may include an amino acid type amphoteric surfactant and a betaine type amphoteric surfactant.

Specific examples of the amino acid type amphoteric surfactant may include a glycine type amphoteric surfactant such as sodium N-lauroyl-N'-carboxymethyl-N'-hydroxyethylethylenediamine (Na lauroamphoacetate), 2-alkyl-N-carboxymethyl-N-hydroxyethylimidazolinium betaine, sodium undecylhydroxyethyl imidazolinium betaine, alkyl diaminoethyl glycine hydrochloride, sodium N-coconut oil fatty acid acyl-N'-carboxyethyl-N'-hydroxyethylethylenediamine, disodium N-coconut oil fatty acid acyl-N'-carboxyethoxyethyl-N'-carboxyethylethylenediamine, disodium N-coconut oil fatty acid acyl-N'-carboxymethoxyethyl-N'-carboxymethylethylenediamine, sodium lauryl diaminoethyl glycine, or sodium palm oil fatty acid acyl-N-carboxyethyl-N-hydroxyethylethylenediamine; an aminopropionic acid type amphoteric surfactant such as sodium laurylaminopropionate, sodium laurylaminodipropionate, or triethanolamine lauryl aminopropionate.

Specific examples of the betaine type amphoteric surfactant may include an aminoacetic acid betaine type amphoteric surfactant such as coconut oil alkyl betaine, lauryldimethylaminoacetic acid betaine, myristyldimethylaminoacetic acid betaine, stearyl dimethyl aminoacetic acid betaine, sodium stearyl dimethyl betaine, coconut oil fatty acid amidopropyl betaine, palm oil fatty acid amidopropyl betaine, lauric acid amidopropyl betaine, ricinoleic acid amidopropyl betaine, or stearyl dihydroxyethyl betaine; and sulfobetaine type amphoteric surfactant such as lauryl hydroxy sulfobetaine.

<Inorganic Salt>

Examples of the inorganic salt may include sodium sulfate. Sodium sulfate has an action of preventing the powder hair dye composition from absorbing moisture and is suitably utilized as an excipient. By containing sodium sulfate, it is possible to suppress a decrease in fluidity caused by moisture absorption, a decrease in storage stability of the oxidation dye, and the like.

<Plant Extract>

Examples of the plant extract may include aloe extract, Scutellaria root extract, Hypericum erectum extract, licorice root extract, beefsteak plant extract, hawthorn extract, rosemary extract, turmeric extract, sea weed extract, burdock extract, ginger extract, mallow extract, tea extract, hamamelis extract, saxifraga extract, citron extract, and soapberry extract.

[Method of Using Powder Hair Dye Composition]

The method of using a powder hair dye composition of the invention includes a step of mixing the powder hair dye composition described above with a liquid medium such as water to prepare a hair dye coating liquid and a step of applying the hair dye coating liquid to the hair.

The liquid medium is preferably water such as tap water, purified water, deionized water, or distilled water or a liquid medium using water as the base. More preferably the liquid medium is water.

The mixing ratio of the powder hair dye composition to the liquid medium is that powder hair dye composition:liquid medium=preferably from 1:5 to 1:15 and more preferably from 1:8 to 1:12 in terms of mass.

The formulation of the hair dye coating liquid is not particularly limited and may be in any form of a liquid form, a cream form, a gel form, or a paste form. It is preferable to prepare the hair dye coating liquid into a cream form or a paste form from the viewpoint of improving ease of handling the hair dye coating liquid with a brush and spreading and adhesive property of the hair dye coating liquid to the hair and of exerting excellent coating operability. In addition, the hair dye coating liquid may be further prepared into a foamy form or a misty form. In the case of preparing into a foamy form, foam may be formed by filling the hair dye coating liquid in a shaking container and shaking the container or a known foaming apparatus such as a non-aerosol foamer or an aerosol foamer may be used.

As a means for applying the hair dye coating liquid to the hair, the hair dye coating liquid may be applied to the hair by using an applicator such as a comb, a brush, or a brush. In addition, the hair dye coating liquid may be applied to the hair with a hand wearing a glove.

For mixing of the powder hair dye composition with the liquid medium, various kinds of preparation tools, for example, a container such as a bottle, a cup, or a tray, a stirring tool such as a stirring rod, and the like can be used. The preparation tool is appropriately selected depending on the viscosity of the mixture and the like. Among the preparation tools, it is suitable to adopt a bottle. In other words, it is possible to easily and quickly mix the respective agents by enclosing the powder hair dye composition and the liquid medium in a bottle at a predetermined ratio and shaking the bottle. Furthermore, it is more suitable to use an applicator container equipped with a bottle and an applicator which is connected to the bottle and discharges the hair dye coating liquid in the bottle. By using such an applicator container, the coating operation becomes simpler since it is possible to prepare the hair dye coating liquid in the bottle and to apply the hair dye coating liquid to the hair by using the applicator. Examples of the applicator equipped in the applicator container may include an applicator in a comb form, a brush form, a nozzle form, or the like. As an applicator, a container with comb with which it is possible to apply the hair dye coating liquid to the hair while combing the hair with the comb is preferable from the viewpoint of handiness.

The leaving time after the hair dye coating liquid being applied to the hair is not particularly limited, but it may be about from 30 to 40 minutes. After the leaving time, the hair dye coating liquid adhered to the hair is washed out. Thereafter, the hair may be properly treated using a shampoo, a conditioner, a treatment, or the like.

EXAMPLES

Hereinafter, the invention will be specifically described with reference to Examples, but the technical scope of the invention is not limited by these Examples.

[Preparation of Powder Hair Dye Composition]

A powder hair dye composition having the composition presented in the following Tables 1 and 2 was prepared, and the powder hair dye composition obtained was subjected to the evaluation on the effect of suppressing a change in the dyed color tone in long-term storage, the fluidity, coating operability of the powder hair dye composition, and the feel of the hair at the time of finishing.

[Evaluation Method]

<Effect of Suppressing Change in Dyed Color Tone in Long-Term Storage>

(Method of Hair Dyeing Treatment) Into a mixing container having a capacity of 100 mL, 3 g of the powder hair dye composition of each Example and Comparative Example and 30 g of water were charged and mixed by using a stirring rod to prepare a hair dye coating liquid. The hair dyeing treatment was performed by applying 3 g of the hair dye coating liquid obtained to 1 g of white hair bundle by using a brush and leaving the hair dye coating liquid for 40 minutes after the coating operation. The hair bundle subjected to the hair dyeing treatment was washed with water and a shampoo to wash out the hair dye coating liquid from the hair bundle, and treated with a conditioner, then the water was wiped off from the hair bundle with a towel, and the hair bundle was dried by using a dryer.

(Evaluation on Effect of Suppressing Change in Dyed Color Tone)

The powder hair dye composition of each example was stored in a constant temperature tank at 50° C. and 80% humidity for 60 days. Using the powder composition of each example stored for a predetermined period of time, the hair dyeing treatment was performed by the method of hair dyeing treatment described above to obtain each hair bundle. In addition, using the powder hair dye composition of each example which was not subjected to the storage treatment, the hair dyeing treatment was also performed in the same manner as the above to obtain each hair bundle, and the hair bundle was used as a control.

Each hair bundle obtained was subjected to visual observation on the presence or absence of a change in the dyed color tone (brightness and saturation of color) depending on the presence or absence of storage treatment by ten panelists under a standard light source and evaluated according to the following criteria.

(Evaluation Criteria)

The observation results were scored in 5 ranks that there was almost no change in the dyed color tone (5 points), there was a significantly slight change in the dyed color tone (4 points), there was a slight change in the dyed color tone (3 points), there was a change in the dyed color tone (2 points), and there was a great change in the dyed color tone (1 point).

Next, the average value of the scored results by the respective panelists was calculated, the effect of suppressing a change in the dyed color tone was judged to be "excellent: 5" when the average value was 4.6 points or more, to be "favorable: 4" when the average value was 3.6 points or more but less than 4.6 points, to be "acceptable: 3" when the average value was 2.6 points or more but less than 3.6 points, to be "slightly poor: 2" when the average value was 1.6 points or more but less than 2.6 points, and to be "poor: 1" when the average value was 1.0 point or more but less than 1.6 points, and the results are taken as the evaluation result.

The evaluation results obtained are presented as the item of "suppression of change in dyed color tone" in Tables 1 and 2.

<Evaluation on Fluidity>

The angle of repose of the powder hair dye composition of each Example and Comparative Example was determined to evaluate the fluidity. The method of measuring the angle of repose is as follows. The angle of repose is the maximum angle of the slope at which stability of the powder is maintained without spontaneous collapse when the powder is piled up in a heap, and the fluidity is higher as the angle of repose is smaller.

(Method of Measuring Angle of Repose)

Into a funnel having a diameter of 10 mm, 50 g of the powder hair dye composition was charged, and the powder hair dye composition was dropped onto a circular plate having a diameter of 60 mm from a height of 200 mm to form a heap of the powder hair dye composition. The angle of repose was measured at four places and the average value thereof was calculated. The results are presented as the item of "angle of repose" in Table 1.

<Evaluation on Coating Operability>

Into a mixing container having a capacity of 100 mL, 3 g of the powder hair dye composition of each Example and Comparative Example and 30 g of water were charged and mixed by using a stirring rod to prepare a hair dye coating liquid. In the operation of applying each hair dye coating liquid to the hair of head of human by using a brush, the operability was evaluated according to the following criteria. The results are presented as the item of "coating operability" in Tables 1 and 2.

5: It is significantly easy to handle hair dye coating liquid with brush and spreading and adhesive property of hair dye coating liquid to hair of head are favorable.

4: It is easy to handle hair dye coating liquid with brush and spreading and adhesive property of hair dye coating liquid to hair of head are favorable.

3: It is possible to handle hair dye coating liquid with brush and spreading and adhesive property of hair dye coating liquid to hair of head are favorable.

2: It is difficult to handle hair dye coating liquid with brush.

1: It is difficult to handle hair dye coating liquid with brush and spreading and adhesive property of hair dye coating liquid to hair of head are insufficient.

<Feel at Time of Finishing>

The hair bundle after being subjected to the hair dyeing treatment was washed with a commercially available shampoo ("Bigen Treatment Shampoo" manufactured by Hoyu Co., Ltd.) and a commercially available rinse ("Bigen Treatment Rinse" manufactured by Hoyu Co., Ltd.) and then dried by using a dryer.

The feel at the time of finishing was evaluated to be "significantly excellent: 5" in a case in which the number of panelists who evaluated the tenderness of the hair-bundle sample to be favorable in two-rank evaluation of favorable and poor was 9 or more among ten expert panelists, to be "excellent: 4" in a case in which the number of panelists was 7 to 8, to be "favorable: 3" in a case in which the number of panelists was 5 to 6, to be "slightly poor: 2" in a case in which the number of panelists was 3 to 4, and to be "poor: 1" in a case in which the number of panelists was 2 or fewer.

The results are presented as the item of "feel at time of finishing" in Tables 1 and 2.

TABLE 1

(Unit: mass %)

| | Example 1 | Example 2 | Example 3 | Example 4 | Example 5 | Comparative Example 1 |
|---|---|---|---|---|---|---|
| (A) Sodium percarbonate | 25 | 12 | 25 | 41 | 25 | 25 |
| (B) Starch | 7 | 10 | 10 | 10 | 26 | 5 |
| (C) m-Aminophenol sulfate | 2 | 2 | 2 | 2 | 2 | 2 |
| (C) 5-Amino-o-cresol sulfate | 2 | 2 | 2 | 2 | 2 | 2 |
| (C) Resorcin | 1 | 1 | 1 | 1 | 1 | 1 |
| (D) Ethylenediamine hydroxyethyl triacetic acid trisodium dihydrate | 2 | 2 | 2 | 2 | 2 | 2 |
| (E) Xanthan gum | 10 | 10 | 10 | 10 | 10 | 10 |
| (E) Sodium carboxymethyl cellulose | 15 | 15 | 15 | 15 | 15 | 15 |
| Disodium lauryl sulfosuccinate | 1 | 1 | 1 | 1 | 1 | 1 |
| Sodium sulfate | 19 | 29 | 16 | — | — | 21 |
| Magnesium stearate | 1 | 1 | 1 | 1 | 1 | 1 |
| p-Phenylenediamine sulfate | 10 | 10 | 10 | 10 | 10 | 10 |
| Toluene-2,5-diamine sulfate | 5 | 5 | 5 | 5 | 5 | 5 |
| Sum | 100 | 100 | 100 | 100 | 100 | 100 |
| Ratio (A/B) of content of component (A) to component (B) | 3.6 | 1.2 | 2.5 | 4.1 | 1.0 | 5.0 |
| Ratio (B/D) of content of component (B) to component (D) | 3.5 | 5.0 | 5.0 | 5.0 | 13.0 | 2.5 |
| Suppression of change in dyed color tone | 3 | 4 | 5 | 5 | 5 | 2 |
| Angle of repose | 37 | 37 | 35 | 35 | 41 | 36 |
| Coating operability | 4 | 5 | 5 | 5 | 5 | 3 |
| Feel at time of finishing | 4 | 5 | 5 | 5 | 5 | 3 |

When Examples 1, 3, and 5 are compared with Comparative Example 1 in Table 1, it is possible to suppress a change in the dyed color tone by setting the content of starch to 7 mass % or more in a powder hair dye composition containing m-aminophenol sulfate, 5-amino-o-cresol sulfate, or resorcin. Furthermore, an excellent effect is acknowledged in the coating operability and feel at the time of finishing. In addition, the effect of improving the fluidity is acknowledged when the content of starch is set to 25 mass % or less.

Furthermore, referring to Examples 2 to 4, it can be seen that the effect of the invention is further exerted and the fluidity is improved by setting the content of sodium percarbonate to 15 mass % or more.

TABLE 2

(Unit: mass %)

| | Example 3 | Example 6 | Example 7 | Example 8 | Example 9 | Example 10 |
|---|---|---|---|---|---|---|
| (A) Sodium percarbonate | 25 | 25 | 25 | 25 | 25 | 25 |
| (B) Starch | 10 | 10 | 10 | 10 | 10 | 10 |
| (C) m-Aminophenol sulfate | 2 | 2 | 2 | 2 | 2 | 2 |
| (C) 5-Amino-o-cresol sulfate | 2 | 2 | 2 | 2 | 2 | 2 |
| (C) Resorcin | 1 | 1 | 1 | 1 | 1 | 1 |
| (D) Ethylenediamine hydroxyethyl triacetic acid trisodium dihydrate | 2 | — | 1 | 3 | 2 | 2 |
| (E) Xanthan gum | 10 | 10 | 10 | 10 | 5 | 20 |
| (E) Sodium carboxymethyl cellulose | 15 | 15 | 15 | 15 | 15 | 15 |
| Disodium lauryl sulfosuccinate | 1 | 1 | 1 | 1 | 1 | 1 |
| Sodium sulfate | 16 | 18 | 17 | 15 | 21 | 6 |
| Magnesium stearate | 1 | 1 | 1 | 1 | 1 | 1 |
| p-Phenylenediamine sulfate | 10 | 10 | 10 | 10 | 10 | 10 |
| Toluene-2,5-diamine sulfate | 5 | 5 | 5 | 5 | 5 | 5 |
| Sum | 100 | 100 | 100 | 100 | 100 | 100 |
| Ratio (A/B) of content of component (A) to component (B) | 2.5 | 2.5 | 2.5 | 2.5 | 2.5 | 2.5 |
| Ratio (B/D) of content of component (B) to component (D) | 5.0 | — | 10.0 | 3.3 | 5.0 | 5.0 |
| Suppression of change in dyed color tone | 5 | 5 | 5 | 4 | 5 | 5 |
| Coating operability | 5 | 5 | 5 | 5 | 5 | 3 |
| Feel at time of finishing | 5 | 3 | 4 | 5 | 5 | 4 |

When Examples 6 and 7 in Table 2 are compared with each other, an effect is acknowledged that the feel at the time of finishing is improved by containing a chelating agent. In addition, when Examples 3, 7, and 8 are compared with one another, it is possible to further enhance the feel of the hair at the time of finishing while suppressing a change in the dyed color tone when the content of chelating agent is from 1 to 3 mass %.

When Examples 3, 9, and 10 in Table 2 are compared with one another, the state of the hair dye coating liquid becomes a state close to a highly hard gel and ease of handling the hair dye coating liquid with a brush and spreading and adhesive property of the hair dye coating liquid to the hair tend to decrease by increasing the content of xanthan gum. Hence, it can be seen that the preferred range of the content of xanthan gum is from 5 to 20 mass %.

INDUSTRIAL APPLICABILITY

The powder hair dye composition of the invention can be utilized as a powder hair dye composition for dyeing body hair such as hair of head, beard, eyebrows, and leg hair of human. In addition to this, the powder hair dye composition of the invention may be utilized for dyeing body hair of an animal such as a pet.

The powder hair dye composition of the invention can be utilized as a powder hair dye composition for beauty parlor or barber shop and a powder hair dye composition for self coloring.

In addition, the method of using a powder hair dye composition of the invention can be utilized for hair dyeing treatment of hair in a beauty parlor, a barber shop or the like and for self coloring.

The invention claimed is:

1. A powder hair dye composition comprising (A) a percarbonate, (B) a starch, and (C) an oxidation dye, wherein
   the powder hair dye composition comprises (B) the starch at from 7 to 25 mass%, and
   (C) the oxidation dye contains at least one selected from m-aminophenol, 5-amino-o-cresol, resorcin, or a salt of m-aminophenol, 5-amino-o-cresol, or resorcin.

2. The powder hair dye composition according to claim 1, wherein a mass ratio (AB) of (A) the percarbonate to (B) the starch is from 0.1 to 10.

3. The powder hair dye composition according to claim 1, further comprising (D) a chelating agent at from 1 to 3 mass%.

4. The powder hair dye composition according to claim 1, further comprising (E) a water-soluble polymer compound (excluding starch) at from 1 to 50 mass%.

5. The powder hair dye composition according to claim 1, further comprising (D) a chelating agent and (E) a water-soluble polymer compound (excluding starch), wherein the powder hair dye composition comprises (A) the percarbonate at 15 mass% or more, (D) the chelating agent at from 1 to 3 mass%, and (E) the water-soluble polymer compound (excluding starch) at from 5 to 50 mass%,
   (E) the water-soluble polymer compound (excluding starch) contains xanthan gum at from 5 to 15 mass%, and
   a mass ratio (B/D) of (B) the starch to (D) the chelating agent is 4.0 or more.

6. A method of using a powder hair dye composition, comprising:
   a step of mixing the powder hair dye composition according to claim 1 with a liquid medium to prepare a hair dye coating liquid; and
   a step of applying the hair dye coating liquid to hair.

7. The powder hair dye composition according to claim 2, further comprising (D) a chelating agent at from 1 to 3 mass%.

8. The powder hair dye composition according to claim 2, further comprising (E) a water-soluble polymer compound (excluding starch) at from 1 to 50 mass%.

9. The powder hair dye composition according to claim 2, further comprising (D) a chelating agent and (E) a water-soluble polymer compound (excluding starch),
   wherein the powder hair dye composition comprises (A) the percarbonate at 15 mass% or more, (D) the chelating agent at from 1 to 3 mass%, and (E) the water-soluble polymer compound (excluding starch) at from 5 to 50 mass%,
   (E) the water-soluble polymer compound (excluding starch) contains xanthan gum at from 5 to 15 mass%, and
   a mass ratio (B/D) of (B) the starch to (D) the chelating agent is 4.0 or more.

10. A method of using a powder hair dye composition, comprising:
    a step of mixing the powder hair dye composition according to claim 2 with a liquid medium to prepare a hair dye coating liquid; and
    a step of applying the hair dye coating liquid to hair.

11. The powder hair dye composition according to claim 1, further comprising (E) a water-soluble polymer compound (excluding starch), wherein (E) the water-soluble polymer compound contains xanthan gum at from 5 to 15 mass%.

* * * * *